United States Patent [19]

Guley et al.

[11] 4,248,856

[45] Feb. 3, 1981

[54] SUSTAINED RELEASE PHARMACEUTICAL COMPOSITIONS

[75] Inventors: Paul C. Guley, Plattsburgh; Richard J. DeNeale, Morrisonville; George Milosovich, Rouses Point, all of N.Y.

[73] Assignee: American Home Products Corporation, New York, N.Y.

[21] Appl. No.: 56,156

[22] Filed: Jul. 10, 1979

[51] Int. Cl.³ .................... A61K 9/22; A61K 9/32; A61K 9/36

[52] U.S. Cl. .................... 424/21; 424/19; 424/32; 424/33; 424/35

[58] Field of Search .................... 424/19–22, 424/35, 32, 33

[56] References Cited

U.S. PATENT DOCUMENTS

| | | | |
|---|---|---|---|
| 2,887,438 | 5/1959 | Cooper et al. | 424/21 |
| 2,991,226 | 7/1961 | Millar et al. | 424/21 |
| 2,993,387 | 7/1961 | Millar et al. | 424/19 X |
| 3,018,221 | 1/1962 | Millar et al. | 424/21 |
| 3,065,143 | 11/1962 | Christenson et al. | 424/19 X |
| 3,133,863 | 5/1964 | Tansby | 424/19 X |
| 3,146,168 | 8/1964 | Battista | 424/19 X |
| 3,147,187 | 9/1964 | Playfair | 424/19 X |
| 3,166,476 | 1/1965 | Lowby | 424/19 X |
| 3,184,386 | 5/1965 | Stephenson | 424/21 |
| 3,266,992 | 8/1966 | de Jong | 424/19 X |
| 3,279,998 | 10/1966 | Raff et al. | 424/19 |
| 3,388,041 | 6/1968 | Gans et al. | 424/21 |
| 3,427,378 | 2/1969 | Henderson et al. | 424/14 |
| 3,558,768 | 1/1974 | Klippel | 424/21 |
| 4,001,390 | 1/1977 | Oano et al. | 424/35 |
| 4,025,613 | 5/1977 | Guy et al. | 424/21 |
| 4,122,157 | 10/1978 | Huber | 424/21 |
| 4,138,475 | 2/1979 | McAinsh et al. | 424/21 |
| 4,140,755 | 2/1979 | Sheth et al. | 424/21 |
| 4,140,756 | 2/1979 | Gallian et al. | 424/21 |

OTHER PUBLICATIONS

West et al., C.A. 85, #103709x (1976).
Davidson et al., C.A. 85, #198101e (1976).
ICI, Ltd., C.A. 89, #95008H (1978).
Dawes et al., C.A. 90, #210054e (1979).
Aellig, C.A. 90, #132966h (1979).
Tuckman, C.A. 90, #142111u (1979).
Lapidus et al., J. Pharm. Sci, 55(8): pp. 840–843, Aug. 1966.
Lapidus et al., J. Pharm. Sci. 57(8): pp. 1292–1301, Aug. 1968.

*Primary Examiner*—Shep K. Rose
*Attorney, Agent, or Firm*—Adley F. Mandel

[57] ABSTRACT

Novel sustained release compositions comprising a core containing a drug, a seal coating surrounding the core and a sugar coating surround the seal coated core are disclosed.

19 Claims, No Drawings

SUSTAINED RELEASE PHARMACEUTICAL COMPOSITIONS

BACKGROUND OF THE INVENTION

1. Field of the Invention

This invention relates to sustained release pharmaceutical compositions and more particularly it relates to sustained release pharmaceutical compositions containing a β-adrenergic blocking agent. Preferably the β-adrenergic blocking agent is propranolol or a pharmaceutically acceptable acid addition salt thereof.

2. Description of the Related Art

During the past few years there has been much work devoted to the development of systems which promote the release of active ingredients over a prolonged period of time. The advantages of administering orally active drugs in a sustained release formulation are numerous. If a drug is released too quickly in the stomach it can conceivably cause stomach upset. Additionally, the acid environment of the stomach may adversely affect the potency of a drug. Also the taking of medication once a day instead of numerous times a day eliminates a major source of inconvenience for the patient as well as providing for a more even distribution of drug concentration in the blood.

One example for the need for sustained release formulations is in the case of 1-(isopropyl-amono)-3-(1-naphthyloxy)-2-propanol (propranolol) described in U.S. Pat. No. 3,337,628. This compound is used in the treatment of coronary artery disease migraine, anxiety, and tremors, and specifically as a β-adrenergic blocking agent. However, a major drawback of compounds disclosed in U.S. Pat. No. 3,337,628 and particularly propranolol is that because of extensive metabolism, little unchanged active material reaches the systemic circulation after oral administration. Additionally, plasma levels of propranolol show a large patient to patient variation. The preparation of a sustained release formulation containing propranolol would allow for less frequent dosing while achieving similar blood levels to those attained by administering smaller doses more frequently.

U.S. Pat. No. 4,138,475 describes a sustained release composition containing propranolol which consists of a hard gelatine capsule containing film coated spheroids. The present invention relates to a new sustained release composition which is not disclosed in, nor rendered obvious by, either of the above cited patents, nor elsewhere in the art.

SUMMARY OF THE INVENTION

According to the present invention, a sustained release composition is provided comprising a compressed core containing a drug, a seal coating surrounding the compressed core and a sugar coating surrounding the seal-coated, compressed core. In addition to a therapeutically effective amount of the drug, the core further comprises hydroxypropyl methylcellulose and ethylcellulose. The seal coating preferably comprises an enteric coating material, and the sugar coating comprises sugar and a loading dose of at least one drug contained in the core. The sugar coating may further contain additional drugs which are not present in the compressed core.

The compressed core is prepared in admixture and preferably from a granulation of the drug and other pharmaceutically acceptable excipients and the seal coating may additionally contain a plasticizer. Thus, the core drug or drugs are substantially free of coating within the compressed core itself. Generally the core drug is a β-adrenergic blocking agent which is mainly used for the treatment of angina pectoris, cardiac arrhythmias, and hypertension. Preferably, the core drug is propranolol, or a pharmaceutically acceptable acid addition salt thereof.

DETAILED DESCRIPTION OF THE INVENTION

The sustained release composition of this invention comprises three main components: a compressed core, a seal coating surrounding the compressed core and a sugar coating surrounding the seal-coated compressed core.

The core formulation, in addition to the drug for which sustained release is desired, comprises about 30% to about 45% by weight of the core of the cellulosic polymers hydroxypropyl methylcellulose and ethylcellulose. The drug, which is preferrably propranolol or a pharmaceutically acceptable acid addition salt thereof, comprises about 29% to about 64% by weight of the core. The ratio of drug to said polymers is in the range from about 0.9:1 to about 2.1:1 and preferrably from about 1:1 to about 1.5:1. Furthermore, the ratio of hydroxypropyl methyl cellulose to ethylcellulose is from about 10:1 to about 1.5:1 and preferrably from about 5:1 to 4:1 to about 1.5:1.

A suitable form of hydroxypropyl methylcellulose is that having a viscosity (2% solution) in the range of 4,000 to 40,000 cps at 20° C., and more particularly a viscosity of 15,000 cps at 20° C. A suitable form of ethylcellulose is that having a viscosity (2% solution) of 5 to 50 cps at 20° C. and more particularly a viscosity of 7 cps at 20° C.

The core formulation may further contain other pharmaceutically acceptable excipients such as binders, fillers, compression aids, lubricants, granulation aids, flow aids and the like.

The seal coating preferably comprises an enteric coating material. These enteric coating materials are materials which are more susceptible to hydrolysis or become soluble at a pH greater than 5. A suitable example of such a material is polyvinylacetate phthalate (PVAP). In order to minimize hardening of a particular coating on aging it is often desirable to employ a plasticizer. In these latter instances the enteric coating material may comprise about 70–100% of the seal coating, and more particularly at least 80% of the seal coating. The seal coating surrounds the compressed core and may be prepared by spray coating the tumbling, compressed cores with a solution of the seal coating.

The seal coated, compressed cores are then sugar coated with a sugar coating suspension or solution comprising sugar and a loading dose of at least one drug contained in the core, for which sustained release properties are desired. The ratio of said drug in the sugar coating to said drug in the compressed core is in the range from about 1:15 to about 1:4.3, more particularly from about 1:8 to about 1:6, and preferably about 1:7. In addition to providing fast release of a therapeutically effective amount of drug and while not completely understood, it appears that the loading dose assists in achieving uniform blood levels of the core drug for which sustained release properties are desired. The sugar coating may further contain drugs not contained in the core, for which sustained release properties are not required.

It has been found that the sustained release composition of this invention appears to be effective at higher densities. More particularly, the composition has a density of at least 1.1, preferably a density of at least 1.2 and most preferrably a density of at least 1.3. While not wishing to be bound by any theory, it is believed that the higher densities assist in minimizing stomach emptying times variations among different patients and in maintaining the composition for longer periods in the upper portions of the alimentary tract from which the drug is better absorbed.

The composition of this invention provides substantially zero order release of the core contained drug for at least 12 hours following the first hour of administration. In the case of the $\beta$-adrenergic blocker, propranolol hydrochloride, the sustained release composition of this invention provides substantially (>80%) the same bioavailability for the drug as provided by the identical dosage of drug administered q.i.d., which is the standard dosage regimen.

The composition of this invention is suitable for those drugs having a short half-life (not greater than about 6–8 hours) which therefore may require more frequent administration. The composition is especially suitable for water-soluble drugs and particularly for $\beta$-adrenergic blocking agents such as propranolol and its pharmaceutically acceptable acid addition salts. Suitable additional drugs employed in the sugar coating include one or more of those drugs which would be utilized in adjunct therapy with the core crug for which sustained release properties are required. For a $\beta$-adrenergic blocking agent such as propranolol such drugs include diuretics, saluretics, vasodilators, alpha beta blockers, ganglionic blockers, centrally acting antihypertensives, inhibitors of the renin-angiotensin-aldosterone system and the like. Illustrative of some of these drugs are hydrochlorothiazide, triamterene, hydralazine, chlorthalidone, furosemide, other thiazide drugs, $\gamma$-[(dimethylamino)methyl]-1,3,4,9-tetrahydro-1-methylpyrano[3,4-b]-indole-1-propanol and its pharmaceutically acceptable salts, spiranolactone, captopril, prazocin, isosorbide dinitrate, isosorbide-2-mononitrate, and the like.

The amount of drug contained in the sustained release compositions of this invention will vary depending on the drug or drugs employed. When, for example, the drug is propranolol hydrochloride, the composition of this invention may contain 40–320 mg., more particularly 80–160 mg.; and the amount of other drugs when employed in the sugar coating but not the core, will vary according to their therapeutically effective amounts.

The invention is further illustrated but not limited by the following examples.

EXAMPLE 1

EXAMPLE 1

| | |
|---|---|
| Propranolol Hydrochloride, U.S.P. | 140. g |
| Mannitol, U.S.P. | 25.5 g |
| Microcrystalline Cellulose, N.F | 36.0 g |
| Talc | 1.00g |
| Ethylcellulose, N.F., 7 cps | 27.4 g |
| Hydroxypropyl Methylcellulose, U.S.P., 90 HG, 15,000 cps | 109.6 g |
| Colloidal Silica | 0.500g |
| Stearic Acid, U.S.P., Purified | 18.0 g |
| Calcium Stearate, N.F. | 2.00g |
| Denatured, 23 A, Alcohol (approx.) | 250 ml |

EXAMPLE 1-continued

| | |
|---|---|
| | 360 mg |

The ethyl cellulose was passed through a mill using a screen and blended with the first seven of the above listed ingredients and most of the stearic acid. The blend was passed through a mill using a screen and then granulated by slowly adding the alcohol and mixing until sufficiently wet. The granulation was then dried, sized and blended with the remaining stearic acid and calcium stearate. The blend was then compressed into 360 mg.cores.

EXAMPLE 2

The compressed cores of Example 1 were seal coated with a sufficient amount of the following coating formulation to add approximately 30 mg. to the weight of the compressed cores after drying.

Polyvinylacetate phthalate (30%) 172 ml Opaseal ® P-28-0200:
Methylene Chloride: 410 ml
Alcohol, Denatured 23 A, Anhydrous: 410 ml
Acetylated glycerides (Myvacet ® 9-40): 8.0 ml

EXAMPLE 3

Dried, seal coated cores of Example 2 where then coated with the following sugar coating suspension containing propranolol hydrochloride in an amount sufficient to add about 20 mg. of the propranolol.

Microcrystalline Cellulose: 0.048 kg.
Sucrose: 0.645 kg.
Water: 0.251 kg.
Propranolol HCl: 0.056 kg.
Titanium Dioxide: 0.006 kg.

The tablets were then further coated with a sugar fillers suspension, a sugar smoothing suspension, a sugar color syrup and a polishing suspension. There was thus obtained a sustained release composition containing about 140 mg. of propranolol hydrochloride in the core and 20 mg. of the drug in the sugar coating.

EXAMPLE 4

Sustained release compositions containing both propranolol HCl and hydrochlorothiazide in the sugar coating were prepared employing the following coating formulations and the seal coated cores of Example 2.

Sucrose: 0.515 kg.
Propranolol HCl: 0.053 kg.
Hydrochlorothiazide: 0.133 kg.
Calcium Carbonate: 0.040 kg.
Water: 0.257 kg.

The tablets were then further coated as in Example 3. There was thus obtained a sustained release composition of propranolol HCl containing 140 mg. of propranolol HCl in the core and 20 mg. of propranolol HCl with 50 mg. hydrochlorothiazide in the sugar coating.

EXAMPLE 5

The dried, seal coated cores of Example 2 were coated with the following sugar coating suspension and as in Example 3 in an amount sufficient to obtain a sustained release composition containing 140 mg. of propranolol HCl in the core, and containing in the sugar coating 20 mg. propranolol HCl, 50 mg. hydrochlorothiazide, and 100 mg. triamterene.

Sucrose: 0.50 kg.
Triamterene: 0.125 kg.

Hydrochlorothiazide: 0.062 kg.
Propranolol HCl: 0.025 kg.
Calcium Carbonate: 0.037 kg.
Water: 0.250 kg.

EXAMPLE 6

Seal coated 180 mg. cores made from the formulation of Example 1 or 210 mg. cores of the following formulation were employed to make sustained release compositions containing 70 mg. propranol in the core and 10 mg. in the sugar coating.

Propranolol Hydrochloride, U.S.P.: 70. g
Calcium Phosphate dibasic (anhydrous): 16.8 g
Microcrystalline Cellulose, N.F.: 31.4 g
Talc: 1.00 g
Ethylcellulose, N.F., 7 cps: 15. g
Hydroxypropyl Methylcellulose, U.S.P., 90 HG, 15,000 cps: 59.8 g
Colloidal Silica: 0.3 g
Stearic Acid, U.S.P., Purified: 14.0 g
Calcium Stearate, N.F.: 2.00 g The following sugar coating suspensions were coated onto the seal coated cores of this example

| Wt. in kg. | A | B | C |
|---|---|---|---|
| Sucrose | .644 | .533 | .512 |
| Propranolol HCl | .056 | .027 | .012 |
| Hydrochlorothiazide | — | .133 | .062 |
| Triamterene | — | — | .125 |
| Microcrystalline Cellulose | .048 | — | — |
| Titanium Dioxide | .0007 | — | — |
| Calcium Carbonate | — | .040 | .037 |
| Water | .251 | .266 | .250 |

Thus were obtained sustained release compositions containing in the sugar coating:

| | D | E | F |
|---|---|---|---|
| Propranolol HCl | 10mg. | 10mg. | 10mg. |
| Hydrochlorothiazide | — | 50 | 50 |
| Triamterene | — | — | 100 |

What is claimed is:

1. A sustained release pharmaceutical composition comprising a compressed core containing a drug, a seal coating surrounding the core and a sugar coating surrounding the seal coated core wherein,
   (a) the core comprises a therapeutically effective amount of at least one drug in an amount of about 29% to about 64% by weight of the core, and the cellulose polymers hydroxypropyl methylcellulose and ethylcellulose in an amount of 30% to about 45% by weight of the core; and
   (b) the seal coating comprises an enteric coating material;
   (c) the sugar coating comprises sugar and a loading dose of at least one drug contained in the core in which the ratio of said one drug in the sugar coating to said one drug in the core is from about 1:15 to about 1:4.3;
   and wherein propranolol or a pharmaceutically acceptable salt thereof comprises at least one drug in both the core and the sugar coating.

2. The composition of claim 1 wherein said one drug is a β-adrenergic blocking agent.

3. The composition of claim 1 or 2 in which the seal coating comprises polyvinylacetate phthalate.

4. The composition of claim 3 in which the ratio of drug in the core to said cellulose polymers is in the range of about 0.8:1 to about 2.1:1 and the ratio of hydroxypropyl methylcellulose to ethylcellulose is in the range of about 10:1 to about 1.5:1.

5. The composition of claim 3 in which the ratio of drug in the core to said cellulose polymers is in the range of about 0.8:1 to about 2.1:1; and the ratio of hydroxypropyl methylcellulose to ethylcellulose is in the range of about 10:1 to about 1.5:1.

6. The composition of claim 1 or 2 in which the ratio of drug in the core to said cellulose polymers is in the range of about 0.8:1 to about 2.1:1 and the ratio of hydroxypropyl methylcellulose to ethylcellulose is in the range of about 10:1 to about 1.5:1.

7. The composition of claim 1 or 2 in which the density of said composition is at least 1.1.

8. The composition of claim 1 or 2 in which the density of said composition is at least 1.2.

9. A sustained release pharmaceutical composition comprising a compressed core, a seal coating surrounding the core and a sugar coat surrounding the seal coated core wherein,
   (a) the core comprises propranolol or a pharmaceutically acceptable acid addition salt thereof in an amount of about 29% to about 64% by weight of the core, and the cellulose polymers hydroxypropyl methylcellulose and ethylcellulose in an amount of about 30% to about 45% by weight of the core;
   (b) the seal coating comprises polyvinylacetate phthalate; and
   (c) the sugar coating comprises sugar and a loading dose of said propranolol.

10. The composition of claim 9 wherein the sugar coating further comprises at least one drug used in adjunct therapy with a β-adrenergic blocking agent.

11. The composition of claim 9 wherein the sugar coating further comprises hydrochlorothiazide.

12. The composition of claim 9 wherein the sugar coating further comprises hydrochlorothiazide and triamterene.

13. The composition of claim 9, 10, 11 or 12 in which the ratio of said propranolol in the sugar coating to said propranolol in the core is in the range of about 1:15 to about 1:4.3; the ratio of said propranolol in the core to said cellulose polymers is in the range of about 0.8:1 to about 2.1:1; and the ratio of hydroxypropyl methylcellulose to ethylcellulose is about 10:1 to about 1.5:1.

14. The composition of claim 13 in which the density of said composition is at least 1.1.

15. The composition of claim 13 in which the density of said composition is at least 1.2.

16. The composition of claim 13 in which the ratio of said propranolol in the sugar coating to said propranolol in the core is in the range of about 1:6 to about 1:8; the ratio of said propranolol in the core to said cellulose polymers is in the range of about 1:1 to about 1:1.5 the ratio of hydroxypropyl methylcellulose to ethylcellulose is about 5:1 to about 1.5:1.

17. The composition of claim 13 comprising about 40-320 mg. of propranolol hydrochloride.

18. The composition of claim 13 comprising about 80-160 mg. of propranolol hydrochloride.

19. The composition of claim 13 comprising about 80-160 mg. of propranol hydrochloride in which the ratio of said propranolol in the sugar coating to said propranolol in the core is about 1:7, the ratio of said propranolol to said cellulose polymers is about 1:1 to about 1.5:1; and the ratio of hydroxypropyl methylcellulose having a viscosity of 15,000 cps at 20° C. to ethylcellulose having a viscosity of 7 cps at 20° C. is about 4:1.

* * * * *